United States Patent [19]

Dougherty et al.

[11] Patent Number: 4,514,174
[45] Date of Patent: Apr. 30, 1985

[54] METHODS FOR POSTERIOR DENTAL RESTORATION EMPLOYING LIGHT CURABLE PACKABLE COMPOSITIONS

[75] Inventors: Emery W. Dougherty, York, Pa.; John B. Heyde, Milford, Del.; Richard J. Bennett, Milford, Del.; Roy L. Smith, Milford, Del.; Louis H. Tateosian; George T. Eden, both of York, Pa.

[73] Assignee: Dentsply Research & Development Corp., Milford, Del.

[21] Appl. No.: 443,154

[22] Filed: Nov. 19, 1982

[51] Int. Cl.³ .............................................. A61C 5/04
[52] U.S. Cl. ................................... 433/226; 433/228
[58] Field of Search ................. 433/226, 228, 217, 39

[56] References Cited

U.S. PATENT DOCUMENTS

| | | | |
|---|---|---|---|
| 3,254,411 | 6/1966 | Shelley | 433/217 |
| 3,709,866 | 1/1973 | Waller | 433/228 |
| 4,089,763 | 5/1978 | Dart et al. | 433/228 |
| 4,226,622 | 10/1980 | Aliotta et al. | 75/25 |
| 4,302,381 | 11/1981 | Omura et al. | 433/228 |
| 4,411,625 | 10/1983 | Koblitz et al. | 433/228 |
| 4,439,380 | 3/1984 | Michl et al. | 433/228 |

FOREIGN PATENT DOCUMENTS 2028855 3/1980 United Kingdom .

*Primary Examiner*—John J. Wilson
*Attorney, Agent, or Firm*—Woodcock, Washburn, Kurtz, Mackiewicz & Norris

[57] ABSTRACT

Novel processes for the restoration of teeth particularly posterior teeth, wherein the use of a matrix band is required, are provided employing one component, packable, actinic light curable, resin-based restorative compositions. Such methods are now capable, for the time, of employing resin-based restoratives in the posterior restoration of teeth wherein the packability of the restorative composition enable the deformation of a matrix to allow substantial restoration of the original conformation of the tooth. Packable one component actinic light curable resin-based restorative compositions are provided.

24 Claims, 7 Drawing Figures

METHODS FOR POSTERIOR DENTAL RESTORATION EMPLOYING LIGHT CURABLE PACKABLE COMPOSITIONS

BACKGROUND OF THE INVENTION

This invention is directed to novel processes for the restoration of teeth, especially posterior teeth. Certain practical considerations apply to the formulation and application of resin based posterior dental restoratives. Accordingly, it is greatly preferred that the restorative composition be effectively homogeneous such that air bubbles or structural discontinuities are substantially avoided from introduction into tooth structure. Additionally, it is greatly preferred that such materials be "packable" and be capable of deforming a matrix band during the course of tooth filling. Such material must also be capable of withstanding the physical stresses extant in the posterior region of the mouth and not crumble, fracture, or erode under such conditions.

It has long been known to employ metallic amalgams in the restoration of posterior teeth. Such amalgam materials have been shown to have good resistance to the physical stresses experienced by posterior teeth and to possess small coeffecients of thermal expansion. Such amalgams have also been demonstrated to have good "packability" and to demonstrate other properties necessary of the posterior restorative. Such materials, however, suffer from uncertainty as to the biological effect of introduction of mercury and other metals in the oral cavity over long periods of time. Additionally, the metallic hue of such restorations is a significant aesthetic detriment.

United Kingdom application GB 2,028,855 published Mar. 12, 1980 discloses a posterior restorative based upon a poly(carboxylic acid) system. Several additional resin based restorative compositions have been proposed for use in the filling of posterior teeth; each of these has demonstrated one or more shortcomings which render them ineffective for such use. Those restorative compositions which have been offered for use in posterior restoration are believed to show substantial physical degradation in use within a relatively short period of time, i.e., about two years, and, accordingly, to be unsuitable for such posterior restorative use. Additionally, such materials are self-curing (autocatalytic), two component systems which require manual mixing prior to use. Such mixing is poorly suited to the attainment of good homogeneity of a restorative since mixing tends to incorporate air into the restorative leading to voids in the restoration and lack of durability.

Those skilled in the art of dental restoration will appreciate that certain posterior restorations, such as Class II restorations, require the employment of a matrix for proper application. Thus, it will be appreciated that the use of a matrix band to surround a tooth to be repaired is generally necessary. More particularly, such bands are needed when the tooth to be repaired must be excavated in such a fashion that the resulting cavity preparation communicates from the top surface to one or more of the side surfaces of the tooth. In such a case, the matrix band is placed around the tooth and held tightly in place while restorative such as amalgam is put into place. The packability of conventional dental amalgams is described, for example, in U.S. Pat. No. 4,226,622 which is incorporated herein by reference.

In interproximal restorations, it is considered vital to so configure the restoration as to attain contact between the restored tooth and the neighboring tooth. Contact is needed for self-cleaning and the avoidance of malocclusion. Such contact has traditionally been attained by contouring the matrix prior to filling with amalgam. Furthermore, amalgam has been packed into the cavity preparation in such a way as further to deform the matrix to ensure the attainment of the original tooth contour and contact with adjacent teeth when appropriate. The foregoing resin based restoratives are not generally capable of being compacted to a degree sufficient to deform a matrix band according to preferred practice. Accordingly, there has been a long felt need for materials and processes for one component resin-based posterior restoration which permits matrix band deformation in practice. Also, there has been a long felt need for resin-based restorative materials which are packable, which eliminate voids and gaps in a restoration, and which better conform to irregularities in the walls of the cavity preparation.

OBJECTS OF THE INVENTION

It is an object of this invention to provide one component, resin-based posterior dental restoratives and methods.

It is another object of the invention to provide light curable, packable restorative compositions which are suitable for use in posterior teeth.

It is a further object to provide such materials which are curable by actinic light, especially visible light.

It is another object to provide methods for the restoration of posterior teeth which are adapted for the maintenance of the external conformation of such teeth.

A further object is to provide such methods employing one component polymerizable compositions which permits deformation of a matrix band during restoration.

A further object is to provide such methods employing polymerizable compositions which are packable and which avoid incorporating areas of inhomogeneity or air bubbles.

A further object is to provide dental restorations and processes for their formation which are physically durable under the stresses extant in posterior teeth.

Other objects will be apparent from a review of the present specification.

SUMMARY OF THE INVENTION

It has been found that a posterior or other tooth in need of restoration can be restored by employing as the filling material a packable, light curable, polymerizable restorative composition comprising a highly filled material. More particularly, such a method has been found which comprises selecting a tooth in need of restoration, said tooth having an original external conformation including a top surface and side surfaces. The tooth is then excavated to form a cavity preparation to be filled, which preparation communicates from the top surface to one or more of the side surfaces of the tooth. The tooth is then surrounded with a deformable matrix band which is then tightened to conform with the general external conformation of the tooth and to cover that portion of the preparation which communicates with the side surfaces of the tooth. The preparation is then filled with a packable, light curable, restorative composition, and the composition compacted in such a fashion that the matrix band is deformed into a configuration which closely approximates the original conformation of the tooth. The composition is then hardened by exposure to actinic light and sculpted as needed to substantially restore the original conformation of the tooth. It is also foreseen that in the extreme the present invention can be used to restore an entire external tooth structure where the tooth has been cut into a stump, a matrix band placed around the entire area being restored, and the materials being placed as a crown on said stump, with a bonding agent especially useful in bonding to dentin, or with appropriate mechanical retention means, such as undercuts or pins, or with both bonding and mechanical retention. It has also been found to provide light curable compositions which are adapted for use in the foregoing methods. Such light curable, packable compositions are also useful in restorations not requiring the use of a matrix band. Thus, compositions have been found which are useful in Class I, Class II, Class III, Class IV and Class V restorations because of their packable nature.

BRIEF DESCRIPTION OF THE DRAWINGS

FIG. 5 depicts the relationship of tooth, void and matrix.

FIG. 6 illustrates the void being filled with restorative so as to deform the matrix.

FIG. 7 shows the restored tooth with hardened restorative in place.

DESCRIPTION OF THE INVENTION

Figure 1:
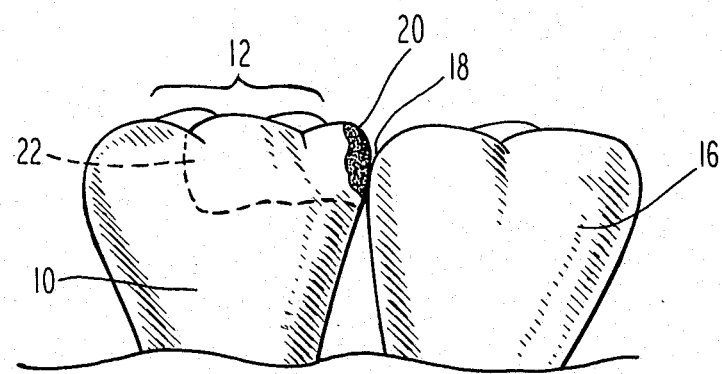
FIG. 1 is a perspective view of a posterior mammalian tooth in need of restoration together with an adjacent tooth.

According to the methods of the present invention, a tooth in need of restoration is identified by the dental clinician. In general, each such tooth will have a top surface and one or more side surfaces. While the present methods may be employed during the conduct of many classes of restoration, restorations involving at least one side surface of a tooth, Class II and Class IV most clearly benefit therefrom. Thus, a tooth which has been identified as being decayed or otherwise in need of restoration is excavated to remove such decay and to form a cavity preparation. In Class II and Class IV restorations, such preparation communicates from the top surface to at least one side surface of the tooth. Those skilled in the art will appreciate that in those cases where restoration of a surface interproximal to an adjacent tooth is necessary, maintenance of the original conformation of the tooth to restore interproximal contact with such adjacent tooth is of great importance.

In general, the restoration of posterior teeth will involve one or more side surfaces together with the top surface of the tooth. In such cases, filling of a tooth proceeds via the opening at the top surface. Thus, a matrix, also called a matrix band, is caused to surround the side surfaces of the tooth to be restored. The matrix band, which is generally a thin, malleable metal or plastic sheet shaped into a truncated cone designed to fit over the side surfaces of the tooth is formed so as to be capable of being tightened about said side surfaces to result in intimate contact therewith. Those skilled in the art will appreciate that numerous matrices are available commercially. It is preferred that an AutoMatrix ™ matrix band (product of the L. D. Caulk Co., division of Dentsply International Inc.) be employed. In those cases wherein the restoration is to comprise a surface which has been in proximal contact with an adjacent tooth, separation of the teeth with, for example, wooden wedges or splints in the conventional way is preferred.

It will be appreciated that where the matrix covers a cavity preparation which has formerly been a convex surface of the tooth, then the matrix will generally be pulled taut across the opening of the preparation. In general, therefore, it is necessary to manipulate the matrix so as to more closely approximate the original contour of the tooth in that area. This has traditionally been done in two stages. Thus, manipulation with pliers or dental instruments may deform the matrix into a shape more closely duplicative of the original contour of the tooth. Additionally, when a tooth is filled with amalgam, the amalgam is compacted in such a way as to deform the matrix band further to cause a substantial return to at least the initial conformation of the tooth. This deformation and restoration of the initial conformation has not been possible with prior resin-based restoratives which have been suggested for posterior use. Only through use of materials in accordance with the present invention in the methods herein disclosed has such deformation of a matrix band been possible. Accordingly, it is now possible to employ resin-based systems for the restoration of posterior teeth which are capable of matrix band deformation and restoration of initial tooth contour. Those skilled in the art will appreciate that this is a significant advance in the art of filling teeth.

Figure 2:
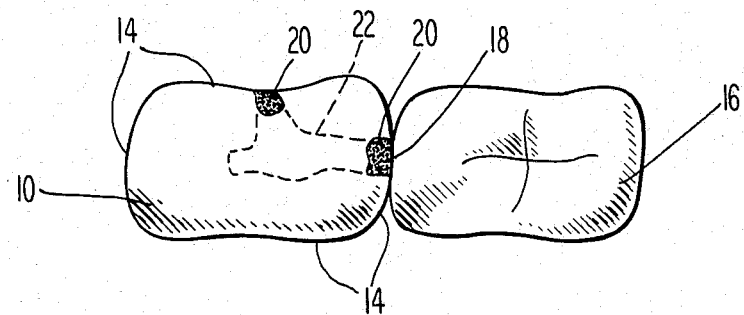
FIG. 2 is a top view of the teeth of FIG. 1.

FIG. 1 depicts a mammalian posterior tooth 10 having need of restoration. Thus, the tooth 10 has a top surface 12 and one or more side surface 14, the top and side surfaces taken together forming an original external conformation of the tooth as depicted. In the FIG. 1 et.seq., the tooth in need of restoration is shown together with an adjacent tooth 16. In the natural state, teeth 10 and 16 are in contact at surface 18. Tooth 10 exhibits decay as depicted in FIGS. 1 and 2. Thus, decay 20 may be detectable superficially by a dentist or through exploratory techniques such as X-ray investigation. Hidden decay may thus be located as shown in phantom 22.

Figure 3:
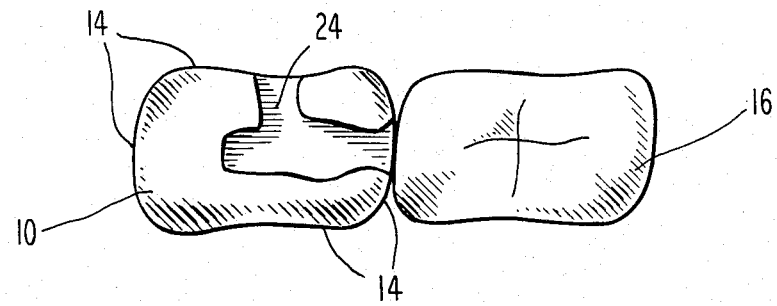
FIG. 3 is a top view of the teeth of FIG. 1 wherein decayed material has been removed to form a void.

As shown in FIG. 3, the decayed material is removed in the conventional way to result in a cavity preparation 24. As depicted, the preparation communicates with one or more side surfaces 14 of the tooth 10; thus the restoration is described as being a Class II restoration. In the Figure, the preparation communicates with the side surface comprising adjacent tooth contact surface 18.

Figure 4:
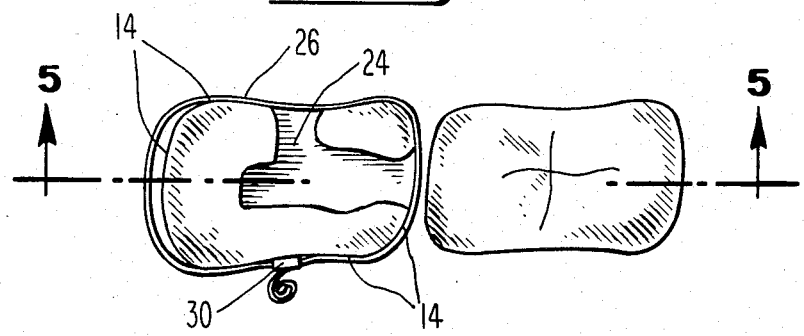
FIG. 4 shows the teeth of FIG. 3 wherein the tooth and the void have been surrounded by a matrix.
Figure 5:
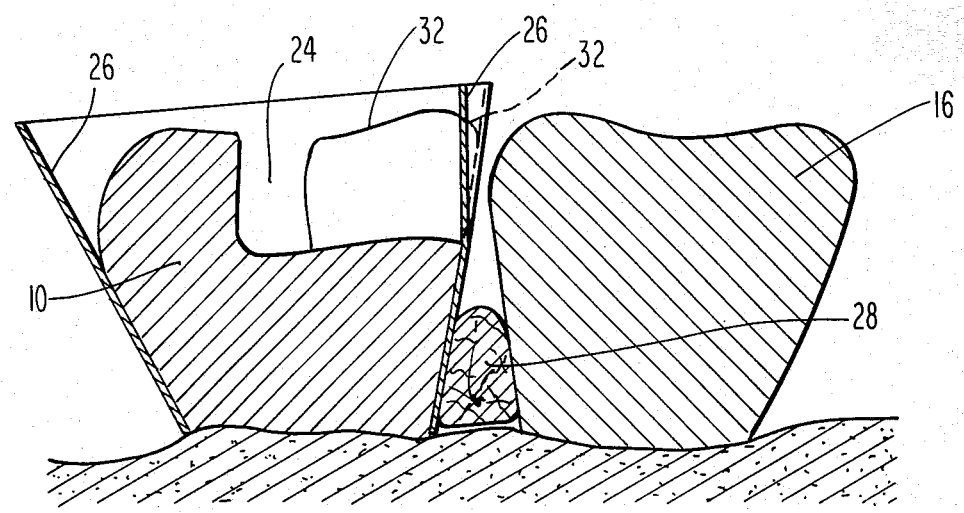
FIGS. 5-7 show vertical cross-sections of the teeth of FIG. 4. Thus.

FIGS. 4 and 5 show the excavated tooth of FIG. 3 surrounded by a matrix 26. Thus, a suitable matrix 26 is caused to surround the side surfaces 14 of the tooth 10. The placement of the matrix is facilitated by employment of a wooden or other wedge 28 in the conventional manner. Preferably, tightening means 30 are employed to tighten the matrix band about the tooth and to cause it to attain the conformation of the excavated area as depicted in FIG. 5. The original conformation of tooth 10 is shown in phantom 32. It will be noted that the matrix band 26 must be deformed during the restoration process to recover the original conformation 32. This deformation is usually accomplished in part by mechanical manipulation of the matrix prior to application of the dental restorative. Final deformation into a close approximation of the original conformation 32 is preferably accomplished through the compacting of restorative in the cavity preparation against the matrix 5 as will be shown.

Figure 6:
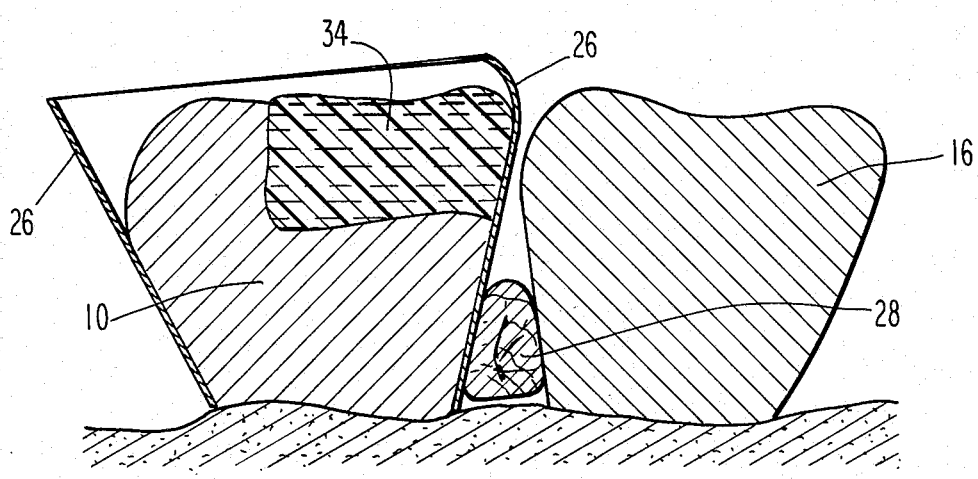
Figure 7:
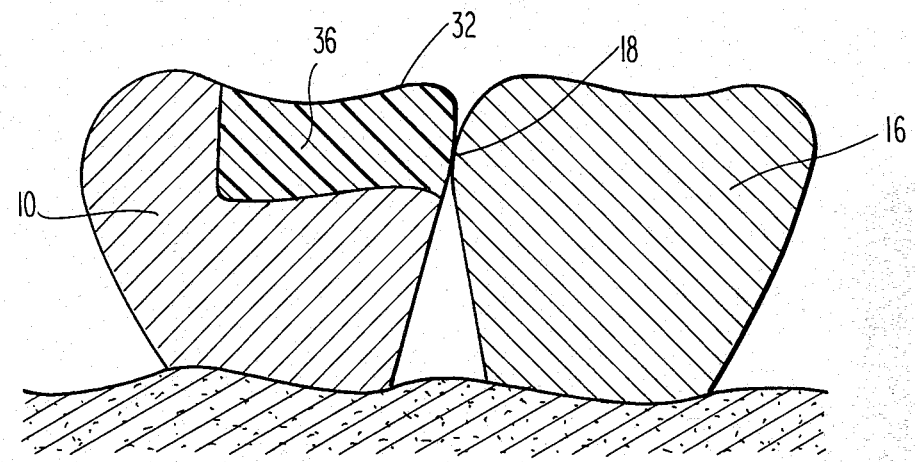

In FIG. 6, packable, light curable dental restorative 34 has been applied to the cavity preparation 24. During the course of application, the packable restorative has been compacted physically. Such compaction was performed in such a way as to transmit compacting forces against the matrix 26 thus causing it to assume the deformed shape shown. This shape is chosen closely to approximate the original conformation of the tooth 32. In general, slightly more restorative is applied than is minimally required to attain the original conformation of the tooth as excess may easily be removed.

While the packable, actinic light curable, posterior dental restoratives useful in the practice of this invention may be inserted into a cavity preparation in any convenient way known to those skilled in the art, it is preferred that the compositions be amenable to injection employing a dental injector. The foregoing preferred composition represents a material which is not only packable and suitable for posterior restoration, but is also amenable to application to a cavity preparation through such injection. The Compules TM system of the L. D. Caulk Division of Dentsply Internatinal Inc. may be employed in the placement of composite restorative materials according to the methods of this invention. Such a placement system allows convenient, precise placement of restoratives without mess or waste. Any other application system, however, may also be employed.

Following application of the restorative, the restorative is hardened by exposure to actinic light or other radiation. Thus, visible, ultraviolet or other radiation is directed upon the restorative which has been so formulated as to be hardenable through such exposure. It will be appreciated that the applicaion, compacting and hardening steps may proceed incrementally to build up a restoration in stages.

Following the hardening of the restorative, the matrix 26 and splint 28 are removed and the hardened restoration 36 reduced conventionally, if necessary, to substantially duplicate the original conformation 32. It is desired that contact surface 18 between teeth 10 and 16 be restored through substantial restoration of the original conformation 32.

In accordance with a preferred embodiment of the present invention, additional steps are undertaken for preparation of the cavities in the teeth to be restored. Such restorative activities improve the overall performance of the system and methods. Thus, exposed dentin surfaces should be treated with a protective material such as Dycal TM offered by the L. D. Caulk Division of Dentsply International Inc. which is known to protect the same from adverse effects caused by contact with restorative materials. The enamel portions of the tooth to be restored should be etched with an acidic medium, such as dilute phosphoric acid or with another material such as Tooth Conditioner sold by the L. D. Caulk Division of Dentsply International Inc. Such conditioning facilitates the bonding of restoratives to the enamel surface. Employment of a bonding agent, especially a light curable bonding agent such as the L. D. Caulk Division's Prisma-Bond TM to the enamel surfaces is also preferred to improve such bonding between the restorative and the tooth. Such bonding agent may be cured simultaneously with the restorative if desired. All of the foregoing modifications are well known, to those skilled in the art.

The restorative materials useful in the practice of the present invention are preferably one component, resin-based, packable materials which may be hardened by irradiation with actinic light. Such material may be applied to the cavity preparation to be filled either incrementally or in bulk and subsequently compacted to deform a matrix and to attain a conformation approximating that of the original tooth. Optionally, and in some applications preferably, the application and restorative may proceed in stages with application and compaction being accomplished sequentially. After the composite has been placed in the cavity to be filled, it is hardened by irradiation with actinic light. Irradiation takes place for sufficient times and at sufficient intensities as to cause substantially complete hardening of the composite restorative. Preferably, such times of irradiation are designed to be convenient for the dental practitioner, preferably less than about 2 minutes. It is preferred that a Prisma-Lite TM or Nuva-Lite TM polymerization units of the L. D. Caulk Co. division of Dentsply International Inc. be employed to effect hardening of the dental restoratives. The application, compaction and hardening of restoratives may take place in a step-wise fashion especially where deep or extensive cavities are to be filled. In such a case, it is also preferred to expose the compacted restorative to actinic light to harden it. This procedure has the additional benefit of hardening the restorative before any viscoelastic flow out of the compacted state can occur. Additionally, avoidance of partial relaxation of the matrix band is largely attained. After the restorative composition has been at least partially hardened by exposure to actinic irradiation, the matrix band is removed. At this time, it is preferred that additional exposure to actinic light be accomplished so that substantially complete hardening of the restorative may be ensured.

The packable, actinic light curable compositions of the present invention are also useful for those restorations not requiring a matrix band, such as Class I, Class III and Class V. In such cases, such material may be applied to the cavity prepration either incrementally or in bulk and subsequently compacted, or with sequential application and compaction and then hardening. The packable nature of the materials of the present invention allows for the elimination of voids and gaps within the cavity by compaction prior to hardening, such as may otherwise occur, because of air trapped in undercut areas or irregularities in the interior surface of the cavity preparation, when compaction is not performed or the material is not packable. With deep or extensive cavities, application, compaction and hardening of the restorative may take place in a step-wise fashion. A stronger restorative is obtained, and there is better resistance to seepage of mouth fluids between the tooth and the restoration.

It is preferred that the restorative material be curable by irradiation with visible light. It has been found that visible light has a substantial transmittance through tooth structure. Accordingly, it is possible and, frequently, preferable to irradiate the polymerizable compositions according to the methods of this invention through one or more tooth surfaces to ensure substantially complete polymerization and hardening of the restorative.

Following the hardening of the dental restorative in the tooth, excess restorative may be removed, if necessary, through the employment of various conventional burs or other dental instrumentation. Polishing is also, preferably, undertaken to result in a smooth, aesthetically pleasing surface.

The restorative compositions usefully employed in the practice of one or more embodiments of the present invention comprise packable, actinic light curable, one component, resin-based materials. More particularly, such materials are capable of being packed when in place in a cavity preparation so as to cause deformation of a matrix and to substantially attain the original conformation of the tooth to be restored.

Those skilled in the art will appreciate that "packability" as that term is used herein, is a quality possessed in greater or lesser degree by dental restoratives. Thus, such persons will appreciate that restorative amalgams are highly packable while commercially available restoratives such as Profile ™, Concise ™, Adaptic ™ and Estilux Posterior ™ (Kulzer) are not. While it is difficult to render an essentially qualitative measure into quantitative terms, an evaluation has been devised which is believed fairly to quantify this factor. Thus, a measure of the resistance to penetration of a composite restorative as given in Example 2 may be used to evaluate packability of the packable, light curable, restorative useful in the practice of this invention. Higher values are to be increasingly preferred. In general, it is desired that such composites have resistance values greater than about 175 g/mm². It is even more preferred that values greater than about 200 g/mm² be exhibited.

In general, those materials which are preferred for use in connection with one or more embodiments of the present invention are photopolymerizable composite dental restorative compositions comprising a polymerizable resin, an amount of a photosensitizer which is sufficient to cause polymerization of said composite dental restoratives upon the application of actinic light thereto and a major proportion of a filler. As described hereinbefore, the materials thus suitable are best described in terms of their packability. The preferred photopolymerizable composite dental restorative of this invention comprises a visible light polymerizable resin, an amount of a photosensitizer sufficient to cause polymerization of the restorative upon the application of actinic light, preferably visible light thereto, and a major proportion of filler in an amount sufficient to cause the restorative to exhibit a resistance to penetration of at least about 175 g/mm². It is even more preferred that the penetration resistance be at least about 200 gm/mm². Preferably the filler (powder of Example 1) is present in a ratio of from abut 3:1 to about 4:1 with respect to resin component (resin blend of Example 1). While no such materials have heretofore been commercially available and none are believed to have been previously known, certain compositions available from the L. D. Caulk division of Dentsply International Inc., have been known under the trademarks NUVA-FIL ™ and PRISMA-FIL ™ which are actinic light curable dental restoratives.

Those skilled in the art having in mind the objects and teachings of this invention, will be able to prepare materials suitable for use in connection with the preferred and other embodiments of this invention from a review of copending U.S. patent applications Ser. No. 318,356 filed Nov. 5, 1981; Ser. No. 323,313 filed Nov. 20, 1981, and Ser. No. 182,624 filed Aug. 29, 1980, each of which are incorporated herein by reference. The best material presently comprehended for use in the practice of the processes of this invention comprises a blend of a visible light polymerizable resin mixture together with a blend of particulate fillers and pigments and is given in Example 1.

EXAMPLE 1

A preferred, packable, visible light curable restorative was formulated from a resin blend comprising:

| | |
|---|---|
| butylated hydroxytoluene (BHT) | 0.025% |
| camphoroquinone | 0.150 |
| fluorescing agent | 0.042 |
| hexamethylene diisocyanate adduct of the diglycidyl methacrylate adduct of bisphenol A (see U.S. Pat. No. 3,629,187, Waller) | 99.280 |
| methyl diethanolamine | 0.500 |
| | 99.997% | and a powder blend comprising:

| | |
|---|---|
| silanated Raysorb T-3000 (Owens Illinois) barium glass filler milled to 2-5 micron mean size silanated with .7% methacryloxypropyl trimethoxy silane | 98.2700% |
| iron oxide pigment | 0.0135 |
| Aerosil R-972 (Degussa) microfine silica filler | 1.7200 |
| | 100.0035% |

The following procedure was carried out at room temperature, about 23° C., under red illumination. The resin blend was formulated by charging a mixing apparatus with the ingredients listed in the order listed and then stirring until all solids are dissolved as determined visually, about 15-30 minutes. The powder was blended by charging a polyethylene container with the ingredients, tumbling for 15 minutes, and then screening twice through a number 8 silk screen. A chromed mixer equipped for vacuum operation was then charged with the resin blend followed by the powder which was smoothed over the resin. 3.4 parts of the powder blend were added to 1 part resin blend. The mixer was closed and a vacuum of 12 mm maintained for 2.5 minutes. The vacuum was reduced to 135 to 140 mm. and kneading carried out for 5 minutes. The mixer was then returned to atmospheric pressure, opened, and any dry powder at the edges pushed into the resin. The mixer was again closed and the pressure reduced to 120 mm. gauge for an additional kneading period of 5 minutes. Mixing being completed, the pressure was returned to atmospheric and the mixer emptied. The visible light curable restorative was packaged and stored at 10° C. or below in light proof containers.

EXAMPLE 2

Another light curable composite resin blend which displays packability in accordance with the present invention is compounded generally in accordance with the procedure of Example 1 except as noted:

| | |
|---|---|
| hexamethylene diisocyanate adduct of the diglycidyl methacrylate adduct of bisphenol A | 24.32% |
| BHT | 0.0061 |
| camphoroquinone | 0.037 |

-continued

| | |
|---|---|
| fluorescing agent | 0.010 |
| methyl diethanolamine | 0.122 |
| Raysorb T-3000 (Owens Illinois) Barium Glass silanated as in Example 1 | 49.10 |
| fumed Silica coated with: | 6.60 |
| 80% diglycidyl methacrylate adduct of bisphenol A (bis-GMA) 20% triethylene glycol dimethacrylate random co-polymer | 19.80 |
| iron oxide pigment | 0.0004 |
| | 100.00% |

The fumed silica is uniformly dispersed throughout the 80% bis-GMA 20% triethylene glycol dimethacrylate comonomers to effect coating of the fumed silica prior to thermal copolymerization. The coated material is then milled to about 25–35 microns. The balance of the materials are then compounded with the coated silica and stored in the dark until use.

EXAMPLE 3

Another restorative composition suitable for the practice of this invention was compounded in a 1 quart Readco sigma blade mixer, heated at 55° C.:

| | Weight % | Component |
|---|---|---|
| | 61.30% | silane Treated Microfine Silica |
| | 0.90 | Aerosil R972 (DeGussa) microfine silica filler |
| | 7.10 | suspension polymerized methyl methacrylate-co-ethylene dimethacrylate (99.8:0.2) |
| | 27.60 | reaction product of hydroxyethylmethacrylate and 2,2,4-trimethyl-hexane-1,6-diisocyanate. |
| | 1.80 | 1,6-Hexanediol dimethacrylate |
| | 0.95 | 3-Methacryloxypropyltrimethoxysilane |
| | 0.09 | camphoroquinone |
| | 0.26 | dimethylaminoethyl methacrylate |
| | 0.003 | pigments |
| Total | 100.00% | |

The Silane treated microfine silica was prepared by silaning 1000 g. 0X50 fumed silica (DeGussa) with 200 g. 3-methacryloxypropyltrimethoxysilane in 12 liters of hexane. The silica and 10 liters of hexane were stirred together for 30 minutes in a stainless steel bucket. Next the silane was added and stirred for one hour. An additional 2 liters of hexane were added and the mixture was allowed to settle for 16 hours. The mixture was decanted, filtered, washed with hexane and dried at 115° C. for 24 hours. The resulting cake was broken up, milled, and sieved through a #10 screen.

The camphoroquinone, dimethylaminoethylmethacrylate, urethane dimethacrylate and 1,6-hexanediol dimethacrylate were blended together and formed into a solution and then added to the mixer. The pigment was compounded with the polymer with a ball mill. The pigmented polymer was added, mixed with the liquid, and allowed to stand for 20 hours to form a preswell. The silanated silica and R972 silica were preblended and added in increments with stirring until a homogeneous mixture was obtained. Finally the silane was added and mixed for 30 minutes. The resulting material is suitable for a posterior filling material, will deform a matrix band, and may be cured with the Prisma-Lite TM visible light polymerization unit to a hard solid. The composition of Example 3 did not discolor when placed and compacted with metallic amalgam placement and compacting instruments.

EXAMPLE 4

The resistance to penetration of various restoratives was evaluated. A cylindrical glass cup 6.5 mm in diameter and 4.5 mm deep was employed to simulate a tooth cavity. The cup together with a plunger having a diameter of 3.2 mm was mounted upon an Instron TM (Instron Co.) force testing machine in such a way that the plunger could be inserted coaxially into the cup. Various restoratives were prepared in accordance with their directions and loaded into the cup to fill the same. The plunger was caused to enter the cup, displacing and/or compacting the restorative. The force needed to penetrate 2.5 mm into the restorative was expressed in $g/mm^2$. The results were as follows:

| | |
|---|---|
| Adaptic TM | <13 $g/mm^2$ |
| Concise TM | <13 $g/mm^2$ |
| Nuva-Fil ® P.A. | 25 $g/mm^2$ |
| Estilux TM | 25 $g/mm^2$ |
| Profile TM | 50 $g/mm^2$ |
| Prisma-Fil TM | 162 $g/mm^2$ |
| Example 1 | 211 $g/mm^2$ |
| Example 2 | 311 $g/mm^2$ |
| Example 3 | 819 $g/mm^2$ |
| Valiant ® (Amalgam) | 1,181 $g/mm^2$ |

EXAMPLE 5

The composition of Example 1 was compared with Profile TM and Estilux TM posterior restoratives and Valiant ® amalgam by applying each to identical excavated proximal typodonts surrounded by matrices. Both the Valiant ® and the material of Example 1 could be compacted to deform the matrix into contact with an adjacent tooth with conventional compacting techniques. Neither the Profile TM nor the Estilux TM materials could be so compacted and matrix band deformation could not be attained by the ordinary compaction of the Profile or Estilux restoratives. A similar procedure employing Prisma-Fil TM (L. D. Caulk Co. division of Dentsply International Inc.) light curable anterior restorative similarly resulted in no substantial deformation of the matrix band.

What is claimed is:

1. A method for the restoration of a tooth comprising:
   selecting a tooth in need of restoration, said tooth having an original conformation having a top surface and side surfaces;
   removing a portion of said tooth to form a cavity preparation, said cavity preparation communicating from said top surface and to at least a first side surface of a said tooth;
   surrounding the side surfaces of said tooth with a matrix, said matrix substantially completely covering said cavity where it communicates with said first side surface;
   applying to said cavity a light curable restorative composition having a resistance to penetration of at least about 175 g./$mm^2$;
   compacting said composition to deform said matrix; and
   hardening said composition by exposure to actinic light
   whereby said original conformation is substantially restored.

2. The method of claim 1 wherein said light is visible light.

3. The method of claim 1 whereby said applying, compacting, and hardening steps are performed, in sequence, a plurality of times.

4. The method of claim 1 wherein said applying step is preceded by the additional step of treating at least a portion of the tooth interior to said cavity with an actinic light curable bonding agent.

5. The method of claim 4 wherein said agent and said composition are hardened simultaneously by exposure to actinic light.

6. The method of claim 4 wherein said treating step is preceded by the additional step of etching at least a portion of the tooth interior to said cavity with an acidic medium.

7. The method of claim 1 wherein said tooth is a posterior tooth.

8. The method of claim 1 wherein said exposure comprises transmitting at least a portion of said light through at least a portion of the tooth.

9. The method of claim 1 wherein said conformation includes a surface in interproximal contact with an adjacent tooth.

10. The method of claim 1 wherein said composition has a resistance to penetration of at least about 200 g/mm$^2$.

11. The method of claim 1 wherein said cavity preparation communicates with at least a plurality of said side surfaces.

12. Method of claim 11 wherein said cavity communicates with at least a portion of each of said side surfaces.

13. The method of claim 1 wherein said light is visible light.

14. A method for the restoration of a tooth comprising:

selecting a tooth in need of restoration;

removing a portion of said tooth to form a cavity preparation;

applying to said cavity preparation a light curable restorative composition having a resistance to penetration of at least about 175 g./mm$^2$; compacting said composition and polymerizing said composition by exposure thereof to actinic light for a time sufficient substantially to harden said composition.

15. The method of claim 14 wherein said light is visible light.

16. The method of claim 14 wherein said applying compacting and polymerizing steps are performed, in sequence, a plurality of times.

17. The method of claim 14 wherein said applying step is preceded by the additional step of treating at least a portion of the tooth interior to said cavity preparation with an actinic light curable bonding agent.

18. The method of claim 17 wherein said agent and said composition are hardened simultaneously by exposure to actinic light.

19. The method of claim 17 wherein said treating step is preceded by the additional step of etching at least a portion of the tooth interior to said cavity preparation with an acidic medium.

20. The method of claim 14 wherein said tooth is a posterior tooth.

21. The method of claim 14 wherein said tooth is an anterior tooth.

22. The method of claim 14 wherein said exposure comprises transmitting at least a portion of said light through at least a portion of the tooth.

23. The method of claim 14 wherein said composition has a resistance to penetration of at least about 200 g/mm$^2$.

24. The method of claim 14 wherein said light is ultraviolet light.

* * * * *